US00PP16338P2

(12) United States Plant Patent
Vanderhaegen

(10) Patent No.: US PP16,338 P2
(45) Date of Patent: Mar. 14, 2006

(54) ***RHODODENDRON* PLANT NAMED 'CLASSIC ROUGE'**

(50) Latin Name: *Rhododendron simsii*
Varietal Denomination: Classic Rouge

(75) Inventor: Johan Vanderhaegen, Kruishoutem (BE)

(73) Assignee: HortiBreed NV, Lochristi (BE)

( * ) Notice: Subject to any disclaimer, the term of this patent is extended or adjusted under 35 U.S.C. 154(b) by 137 days.

(21) Appl. No.: 10/782,636

(22) Filed: Feb. 19, 2004

(51) Int. Cl.
*A01H 5/00* (2006.01)

(52) U.S. Cl. ..... Plt./240

(58) Field of Classification Search ..... Plt./240, Plt./239, 238
See application file for complete search history.

*Primary Examiner*—Kent L. Bell
(74) *Attorney, Agent, or Firm*—Mark P. Bourgeois

(57) ABSTRACT

A new cultivar of *Rhododendron* plant named 'Classic Rouge' that is characterized by dark shiny green leaves, continuous flowering for 6 weeks, vigorous growth and large red flowers. In combination, these traits set 'Classic Rouge' apart from other known existing varieties of *Rhododendron* known to the inventor.

1 Drawing Sheet

Botanical classification: *Rhododendron simsii.*
Variety denomination: 'Classic Rouge'.

BACKGROUND OF THE INVENTION

The present invention relates to a new and distinct cultivar of *Rhododendron* plant botanically known as *Rhododendron simsii* and hereinafter referred to by the cultivar name 'Classic Rouge'.

The new cultivar is the product of a breeding program conducted by the inventor in a cultivated area of Kruishoutem, Belgium. The objective of the breeding program is to develop new *Rhododendron* cultivars with interesting and unique flower and foliage colors and long flower longevity.

'Classic Rouge' is a hybrid that originated from the hybridization of the female or seed parent *Rhododendron* 'Friedhelm Scherrer' (not patented) and the male or pollen parent *Rhododendron simsii* 'Desiree' (not patented). The cultivar 'Classic Rouge' was selected by the inventor in April of 1992 as a single plant within the progeny of the stated cross in Kruishoutem, Belgium.

Asexual reproduction by cuttings of the new cultivar 'Classic Rouge' were taken in November 1992 in Kruishoutem, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Rhododendron* cultivar 'Classic Rouge'. These traits in combination distinguish 'Classic Rouge' as a new and distinct cultivar apart from all other existing varieties of *Rhododendron* known to the inventor.

1. *Rhododendron* 'Classic Rouge' exhibits dark shiny green leaves.

2. *Rhododendron* 'Classic Rouge' exhibits flowers for a 6 week period.
3. *Rhododendron* 'Classic Rouge' exhibits vigorous growth.
3. *Rhododendron* 'Classic Rouge' exhibits large red flowers.

The new cultivar 'Classic Rouge' is distinguishable from the female parent *Rhododendron* 'Friedhelm Scherrer' by the following characteristics:

1. 'Classic Rouge' flowers for 6 weeks, 'Friedhelm Scherrer' flowers for 2 weeks.
2. 'Classic Rouge' has darker red flowers.

The new cultivar 'Classic Rouge' is distinguishable from the male parent *Rhododendron* 'Desiree' by the following characteristics:

1. 'Classic Rouge' is more resistant to leaf drop.
2. 'Classic Rouge' has larger flowers.
3. 'Classic Rouge' is more susceptible to damage by frost.

BRIEF DESCRIPTION OF THE DRAWING

The accompanying photograph illustrates the distinguishing traits of *Rhododendron* 'Classic Rouge'. The plant in the photograph shows an overall view of a 24 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Rhododendron* cultivar named 'Classic Rouge'. Data was collected in Kruishoutem, Belgium from 24 month old greenhouse grown plants in 1.0 liter containers. The time of year was Winter and the average temperature was 18° Centigrade during the Summer and 4° Centigrade during the Winter. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Classic Rouge' has not been tested under all possible conditions and phenotypic differences may be observed with variations in environmental, climatic, and cultural conditions, however, without any variance in genotype.

Botanical classification: *Rhododendron* 'Classic Rouge'.
Use: Ornamental Perennial Shrub.
Parentage: 'Classic Rouge' is a hybrid plant that resulted from the induced hybridization of the following parent plants:
*Female parent.*—*Rhododendron simsii* 'Friedhelm Scherrer'.
*Male parent.*—*Rhododendron simsii* 'Desiree'.
Vigor: Low to moderate.
Growth rate: Approximately 4.7 cm. per year.
Growth habit: Broad Upright, densely branched.
Plant shape: Flattened globular.
Suitable container size: 1.0 liter container.
Height: 23 cm. in height.
Width: 39 cm. in width.
Hardiness: USDA Zone 9.
Propagation: Cuttings.
Time to initiate roots: Approximately 30 days to produce roots on an initial cutting.
Time to produce a rooted cutting or liner: Approximately 60 days.
Root system: Fine and fibrous.
Stem:
*Branching habit.*—Freely branching.
*Average number of lateral branches.*—25.
*Pinching.*—No.
*Lateral branch diameter.*—2.5 cm. in diameter.
*Lateral branch length.*—9.3 cm. in length.
*Lateral branch strength.*—Moderately strong.
*Stem color.*—144A to 144B, older stems 200C to 200D.
*Pubescence.*—Strong, length 1 mm, color gray-orange 174B.
*Internode length.*—6.7 mm. between nodes.
*Shape.*—Round.
*Surface.*—Dull.
*Stem strength.*—Moderately strong.
Foliage:
*Texture.*—Glossy, slightly leathery.
*Leaf arrangement.*—Alternate, clustered towards the top of the stems.
*Compound or single.*—Single.
*Quantity of leaves per lateral branch.*—14.
*Leaf shape.*—Elliptic to Obovate.
*Leaf apex.*—Rounded.
*Leaf base.*—Attenuate.
*Leaf length.*—3.5 cm. in length.
*Leaf width.*—1.9 cm. in width.
*Pubescence.*—Slight, both sides, length 1 mm, color gray-orange 165B to 165C.
*Leaf margin.*—Entire.
*Vein pattern.*—Pinnate.
*Young leaf color* (*upper surface*).—Between 137A and 147A.
*Young leaf color* (*lower surface*).—Between 138A and 146B.
*Mature leaf color* (*upper surface*).—Between 139A and 189A.
*Mature leaf color* (*lower surface*).—137C.
*Vein color* (*lower surface*).—144A to 144B.
*Vein color* (*upper surface*).—144A to 144B.
*Leaf attachment.*—Petiolate.
*Petiole dimensions.*—5 mm in length, slightly flattened 2.5 mm. in width.
*Petiole color.*—144A.
*Durability of foliage to stress.*—High.
Flower:
*Flower arrangement.*—Terminal clusters.
*Inflorescence type.*—Semi-double.
*Inflorescence dimensions.*—7.5 cm. in diameter and 3.6 cm. in height.
*Flowering habit.*—Continuously once a year.
*Flower form.*—Hose in hose.
*Quantity of flowers per lateral stem.*—Approximately 5.
*Quantity of flower buds per lateral stem.*—Approximately 5.
*Quantity of flowers and buds per plant.*—Approximately 125.
*Flowering season.*—Late winter to early summer.
*Time to flower or response time.*—10.5 months.
*Rate of flower opening.*—After the first flower of a cluster has opened, all flowers of that cluster will open in approximately 14 days.
*Fragrance.*—None.
*Self-cleaning or persistent.*—Self-cleaning.
*Flower bud length.*—1.5 cm. in length.
*Flower bud diameter.*—8 mm. in diameter.
*Flower bud shape.*—Ovate.
*Bud color.*—145A to 145B.
*Rate of bud opening.*—10 days.
*Flower aspect.*—Upright to outward.
*Flower shape.*—Funnelform.
*Flower dimensions.*—5.9 cm. in diameter and 3.6 cm. in height.
*Flower longevity.*—Lasts approximately 42 days on plant.
*Petal appearance.*—Dull, slight velvety.
*Petal texture.*—Glabrous.
*Petal arrangement.*—Funnelform, petals placed rotate.
*Number of petals.*—Five in number.
*Petals fused or unfused.*—Lower 25% fused.
*Petal shape.*—Obovate.
*Petal margin.*—Entire, wavy.
*Petal apex.*—Rounded to praemorse.
*Petal dimensions.*—4.1 cm. in length and 2.8 cm. in width.
*Petal color when opening* (*upper side*).—57B with a darker center 57A to 61C.
*Petal color when opening* (*under side*).—57B, with a darker center 57A to 61C.
*Petal color when fully opened* (*upper side*).—57A to 57B, the upper petal has a macule at the base 53A to 53B covering 60% of the petal with a darker center 57A to 61C.
*Petal color when fully opened* (*under side*).—61C.
*Petal color fading to.*—Not fading.
*Petaloid appearance.*—Dull, slightly velvety.
*Petaloid arrangement.*—Rotate, in the center of the flower.
*Petaloid number.*—5 in number.
*Petaloid shape.*—Irregular, obovate to flabellate.
*Petaloid margin.*—Entire.

*Petaloid dimensions.*—3.0 cm. in length and 1.3 cm. in width.
*Petaloid color immature.*—57A to 57B.
*Petaloid color mature.*—57A to 57B.

Calyx:
*Calyx shape.*—Funnelform.
*Calyx dimensions.*—3.6 cm. in length and 5.9 cm. in width.

Bracts:
*Number of bracts.*—5 in number.
*Bract dimensions.*—2.9 cm. in length and 2.2 cm. in width.
*Bract shape.*—Obovate to incised.
*Bract apex.*—Rounded.
*Bract base.*—Broad Cuneate.
*Bract margin.*—Entire.
*Bract pubescence.*—Sparse on under side, length 1.0 mm, color 155B.
*Bract color* (*upper side*).—61C, with a darker base 53B to 60A.
*Bract color* (*under side*).—57C to 61C.

Pedicels:
*Pedicel dimensions.*—8.0 mm. in length and 1.5 mm. in diameter.
*Pedicel angle.*—75°.
*Pedicel color.*—145B.
*Pedicel pubescence.*—Strong, length 0.5 mm, color yellow-green 150D.
*Pedicel strength.*—Moderate.

Reproduction organs:
*Stamen number.*—2.
*Anther shape.*—Dorsifixed, oval.
*Anther dimensions.*—1.5 mm.
*Anther color.*—183A.
*Filament length.*—1.8 cm.
*Filament color.*—61C.
*Amount of pollen.*—Very low.
*Pistil number.*—1 in number.
*Pistil dimensions.*—2.5 cm. in length.
*Stigma shape.*—Club shaped, flattened at the top.
*Stigma color.*—181A.
*Style length.*—2.45 mm.
*Style color.*—57A.
*Ovary color.*—144B to 144C.

Seed: Seed production has not been observed.

Disease resistance: Plants of the new *Rhododendron* have not been observed for disease resistance.

Pest resistance: Plants of the new *Rhododendron* have not been observed for pest resistance.

It is claimed:

1. A new and distinct variety of *Rhododendron* plant named 'Classic Rouge' as described and illustrated.

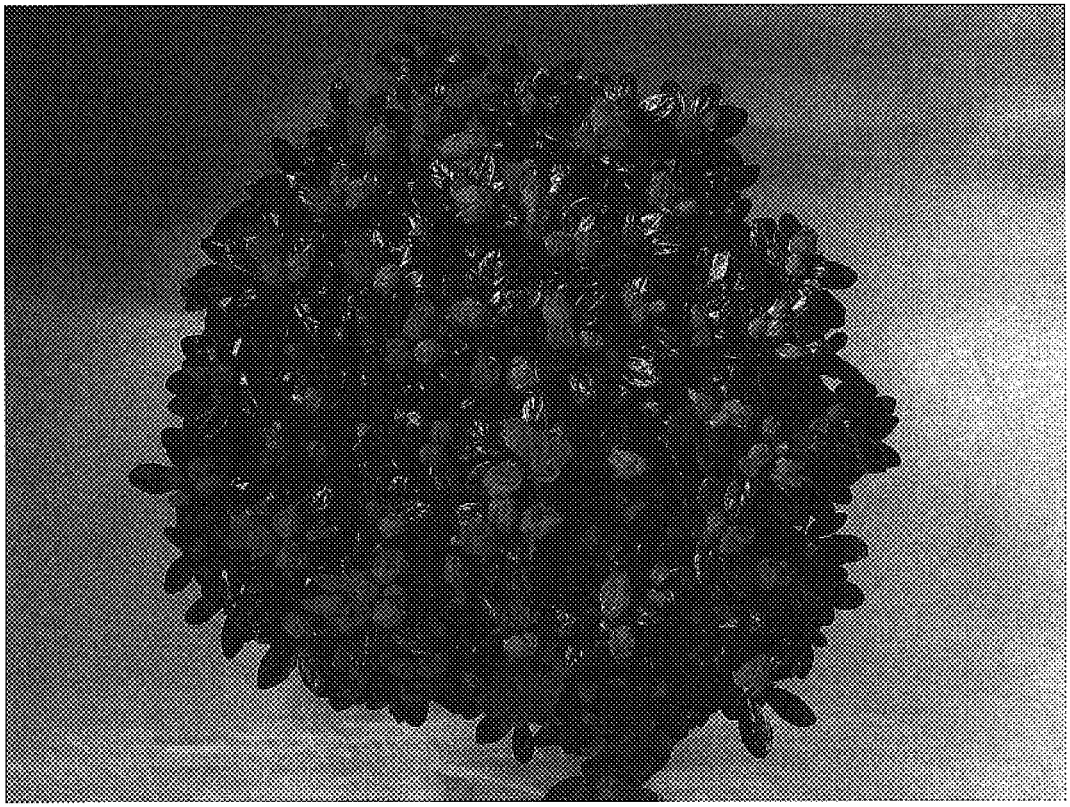

* * * * *